United States Patent
Espinosa

(10) Patent No.: US 6,631,650 B1
(45) Date of Patent: Oct. 14, 2003

(54) THIEF SAMPLING PROBE

(75) Inventor: Kris Espinosa, Longmont, CO (US)

(73) Assignee: Geneva Pharmaceuticals, Inc., Princeton, NJ (US)

(*) Notice: Subject to any disclaimer, the term of this patent is extended or adjusted under 35 U.S.C. 154(b) by 217 days.

(21) Appl. No.: 09/629,278

(22) Filed: Jul. 31, 2000

(51) Int. Cl.[7] .............................................. G01N 1/00
(52) U.S. Cl. .................................................. 73/864.44
(58) Field of Search ....................... 73/864.44, 864.45, 73/864.62, 864.74; 175/20, 58

(56) References Cited

U.S. PATENT DOCUMENTS

| | | | |
|---|---|---|---|
| 2,283,650 A | * 5/1942 | Sanborn | |
| 3,326,049 A | * 6/1967 | Eley | 73/864.44 |
| 4,062,386 A | * 12/1977 | Zanasi | 141/258 |
| 4,116,247 A | * 9/1978 | Zanasi | 141/392 |
| 4,549,612 A | * 10/1985 | Cushing | 73/864.44 |
| 5,474,140 A | * 12/1995 | Stevens | |
| 5,476,017 A | * 12/1995 | Pinto et al. | 73/864.62 |
| 5,703,301 A | 12/1997 | Pinto et al. | 73/864.63 |
| 5,996,426 A | 12/1999 | Robinson et al. | 73/864.63 |

OTHER PUBLICATIONS

Berman et al., vol. 21(11), "Blend Uniformity and Unit Dose Sampling," pp. 1257–1283 (1995).
Chowhan, Z.T., "Sampling of Particulate Systems," pp. 48–55 (1994).
Powder Tech., vol. 1, Industrial Solids Mixers, p. 101, (1967).
Berman et al., Drug Development and Industrial Pharmacy, vol. 22(11), "Unit Dose Sampling: A Tale of Two Thieves," pp. 1121–1132 (1996).
Kraemer et al., Drug Development and Industrial Pharmacy, vol. 25(2), "Sampling Bias in Blending Validation and a Different Approach to Homogeneity Assessment," pp. 217–222 (1999).
Crowder et al., Pharmaceutical Technology, "The Physics of Powder Flow Applied to Pharmaceutical Solids," pp. 50–54 (2000).
Carstensen et al., Drug Development and Industrial Pharmacy, vol. 22(4), "Blending Validation and Content Uniformity of Low–Content, Noncohesive Powder Blends," pp. 285–290 (1996).
Muzzio et al., Pharmaceutical Technology, "An Improved Powder–Sampling Tool," pp. 92–110 (1999).
Pastor et al., Pharmaceutical Technology, Yearbook 1999, "A Novel Sample Thief Dsigned to Avoid Biased Data," pp. 47–54 (1999).
Kaye, B.H., Powder and Bulk Engineering, "Sampling and Characterization Research: Developing Two Tools for Powder Testing," (Feb. 1996).
Hwang et al., Pharmaceutical Technology, "Evaluation of Blend Sampling Errors: A Statistical Approach," pp. 56–65, (Jun. 1999).
Memo from PDA, Inc.,Subject: FDA Comments on Technical Report No. 25, Sep. 4, 1997.

* cited by examiner

Primary Examiner—Robert R. Raevis
(74) Attorney, Agent, or Firm—Lydia T. McNally

(57) ABSTRACT

A sample thief comprising: an outer hollow rod with an open end; a piston with a plunger end inserted within the outer hollow rod; and the outer hollow rod having an adjustable means. The thief operates by inserting the thief into a blend to be sampled just above the area of the blend to be sampled; adjusting the plunger so that a cavity greater than the desired sample size is created; compacting the sample into the thief; removing the thief from the blend; ejecting the excess sample to a predetermined point; and collecting the sample.

5 Claims, 4 Drawing Sheets

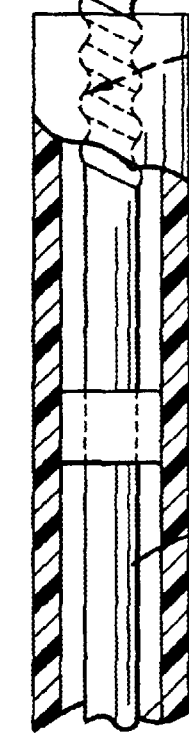
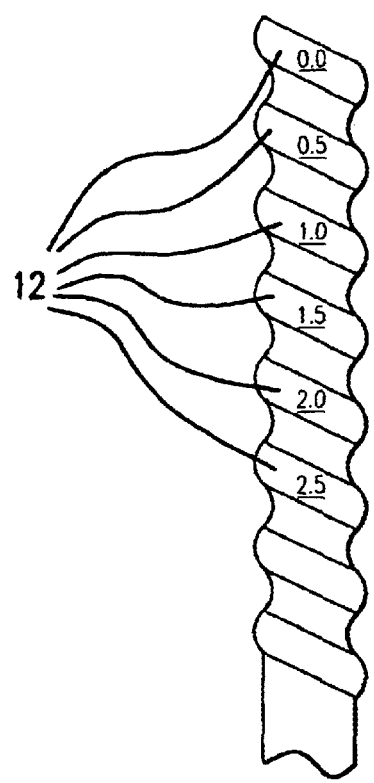
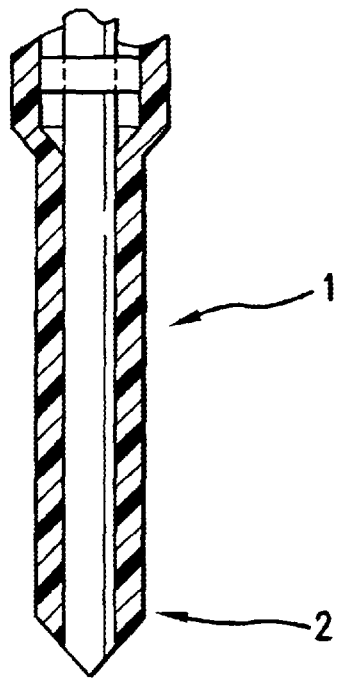
FIG. 3
FIG. 4

THIEF SAMPLING PROBE

BACKGROUND OF THE INVENTION

Under the Federal Food, Drug and Cosmetic Act, a drug is considered adulterated if it is not produced in conformance to Current Good Manufacturing Practices (CGMP's). CGMP's are defined in 21 Code of Federal Regulations, Parts 210 and 211. Under these regulations, the manufacturers of pharmaceutical products are required to validate their manufacturing processes. A properly validated process provides a high degree of assurance that the resulting product consistently meets predetermined specifications and quality characteristics. For a solid dosage form or compressed tablet, process validation must demonstrate the uniformity of the final powder blend as well as the drug product. In 1993, as a result of a court ruling in United States v. Barr Laboratories, 812 F. Supp. 458 (D.N.J. 1993), this aspect of validation received increased attention from both the industry and the Food and Drug Administration (FDA).

As a result of this court decision, and FDA's 1996 proposal to amend CGMP regulations to include routine testing of blend homogeneity, the pharmaceutical industry has been faced with the challenge of collecting samples that are truly representative of the final blend. Attempts to develop effective sampling methodology have been frustrating. Presently used methods continue to produce sampling errors on susceptible blends. Often the relative standard deviation ("RSD") of the blend samples is significantly higher than the RSD of the finished product content uniformity results. Some products also tend to show a high or low assay bias on blend sampling that is not reproduced in the finished product test results. As FDA is requiring unit blend testing on all new NDA and ANDA filings, sampling issues continue to be a significant problem.

Currently there are many different sampling systems used to sample blends. One such system is a powder thief which is designed based on the thieves used to sample grains. The technique for sampling with the grain type thief consists of the sampler or operator inserting the thief tip into the powder bed just beyond the sampling location with the port closed. The port is then opened and the thief is rotated or shaken to cause the sample to enter the chamber. The port is then closed and the sample is withdrawn and transferred to a bottle.

However, because grain, unlike pharmaceutical blends, is fairly homogenous it does not segregate based on the properties for which it is being sampled (e.g. mold contamination). Pharmaceutical blends are generally powders of different size, density, shape and cohesiveness. They may be granulated, which helps to maintain homogeneity, once achieved, by "gluing" the various ingredients together in granules. In contrast to granulated samples, in direct blends the various ingredients remain free to flow, remix, and demix according to their individual properties. Direct blends have a tendency to segregate when the powder bed is disturbed. Accordingly, there are several problems associated with using the above design for sampling pharmaceutical direct blends. For example, the entry of the thief into the blend disturbs the bed, causing localized mixing or segregation, depending upon the properties of the blended powders. Another problem arises because only a small portion of the blend is required to flow into the sampling port. The flow is thus selective, based on the physical characteristics of the individual ingredients noted above. Electrostatic forces can also cause very fine powders to adhere to the inside of the sampling port as the sample is removed from the thief.

With state-of-the-art powder thieves, the noses of the thieves precede the sampling ports as they are inserted into the powder bed. This causes additional mixing or segregation. The sampling ports, which open perpendicular to the line of entry into the powder bed, require that the granulation be caused to flow into the opening, assisted by rotation of the thief. This places a burden of reproducibility on operator technique and is frequently the source of sampling phenomena. Additionally, they are designed such that the operator must disassemble the thief and remove the sample port in order to transfer the sample to a bottle.

SUMMARY OF THE INVENTION

The present invention overcomes these major sampling issues and allows for samples that are representative of the final blend. One embodiment of the thief of the present invention is shown in FIG. 3. The technique for sampling with the thief of the present invention consists of the sampler or operator inserting the thief tip to the sampling location with the cavity plugged. The plug is retracted and the thief is inserted a short distance further into the sample, packing the blend in the cavity and forming a plug of sample. The thief is withdrawn and the plug of sample is partially ejected to a predetermined point. The end of the plug of sample is sliced off and discarded. The remaining plug comprises the sample.

In the thief of the present invention, the sampling cavity resides at the tip of the thief so that the thief has not previously disturbed the area to be sampled. The material in front of the sampling cavity is forced into the cavity intact and compressed into a plug. Removal of the sample is by quick ejection of the plug intact. The influences of operator technique and differences in ingredient physical characteristics are greatly minimized. In addition, removal of the sample is quick and easy.

BRIEF DESCRIPTION OF THE DRAWINGS

FIG. 3 is a schematic of the outer hollow rod with inner piston of the thief of the present invention.

FIG. 4 is a schematic of a bisection of the screw threads of a worm/screw type locking mechanism.

DETAILED DESCRIPTION OF THE PRESENT INVENTION

Figure 1:
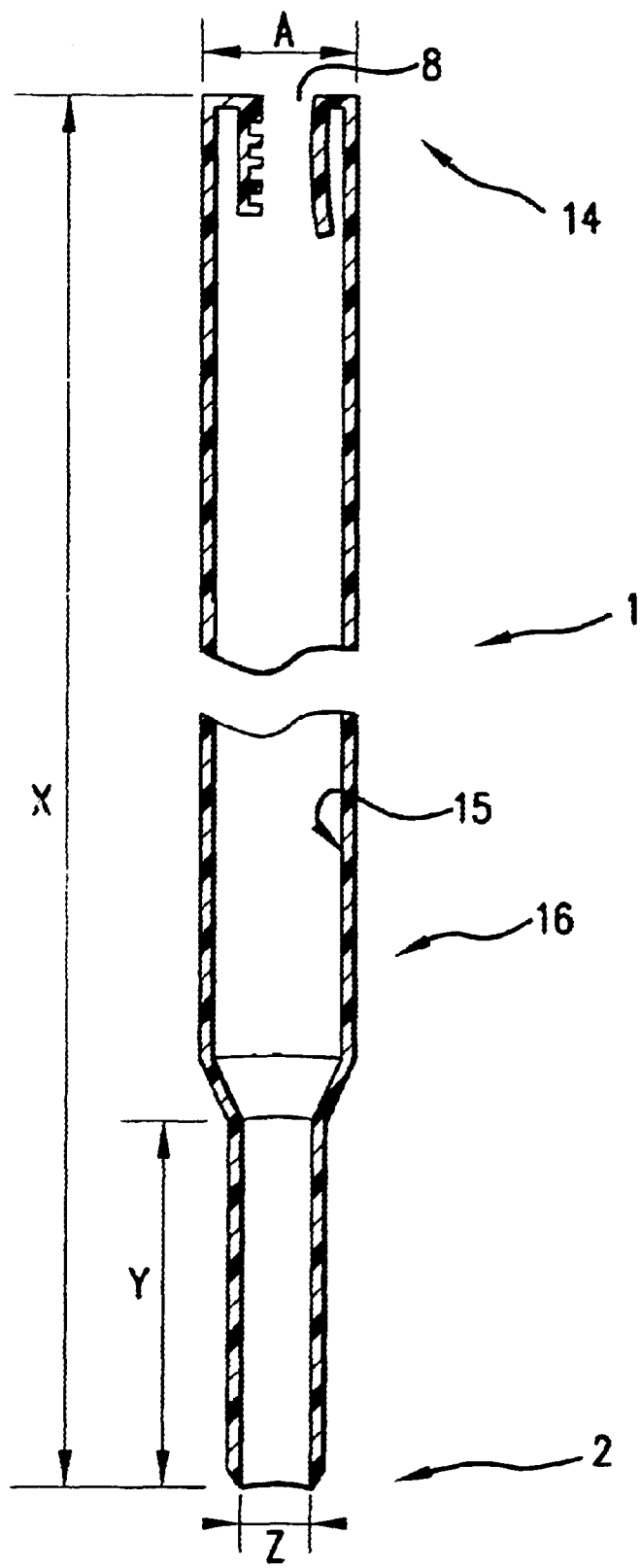
FIG. 1 is a schematic of the outer hollow rod of the thief of the present invention.

The present invention is a sampling thief. FIG. 1 is a schematic of the outer hollow rod 1 of the sampling thief.

The outer hollow rod 1 has a top end 14 and a bottom end 2. The bottom end 2 is also known as the tip. Outer hollow rod 1 also has an inner surface 15 and an outer surface 16. The length X of the outer hollow rod 1 is the length needed to reach into the area to be sampled. In one embodiment the length X is about 3 to 4 feet, preferably 3 feet. The length Y can be any length shorter than X, preferably 10 cm. The bottom end 2 of outer hollow rod 1 is open. Preferably the opening may be beveled which reduces the ability of large particles to avoid entrapment in the sample chamber. The size of the opening Z is the smallest diameter that will give enough strength to allow the bottom end 2 to be forced into the proper depth in the powder bed to be sampled. In one embodiment Z can be 0.1–1.0 cm, preferably 0.5 cm. The diameter of the larger end a of outer hollow rod 1 can be any width larger than the diameter of Z, preferably four times as large as Z, or 0.4–4 cm. The larger end a of outer hollow rod 1 consists of a locking type mechanism. This locking mechanism can be any type of locking mechanism, and will be discussed below.

Figure 2:
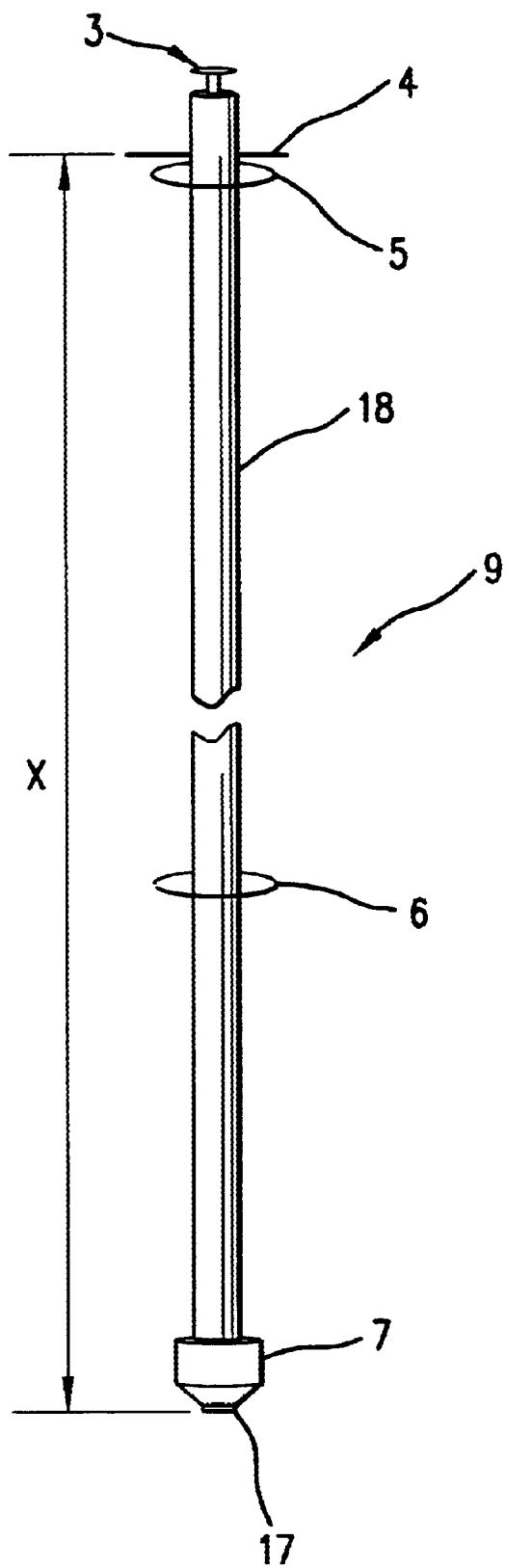
FIG. 2 is a schematic of the inner piston of the thief of the present invention.
Figure 5:
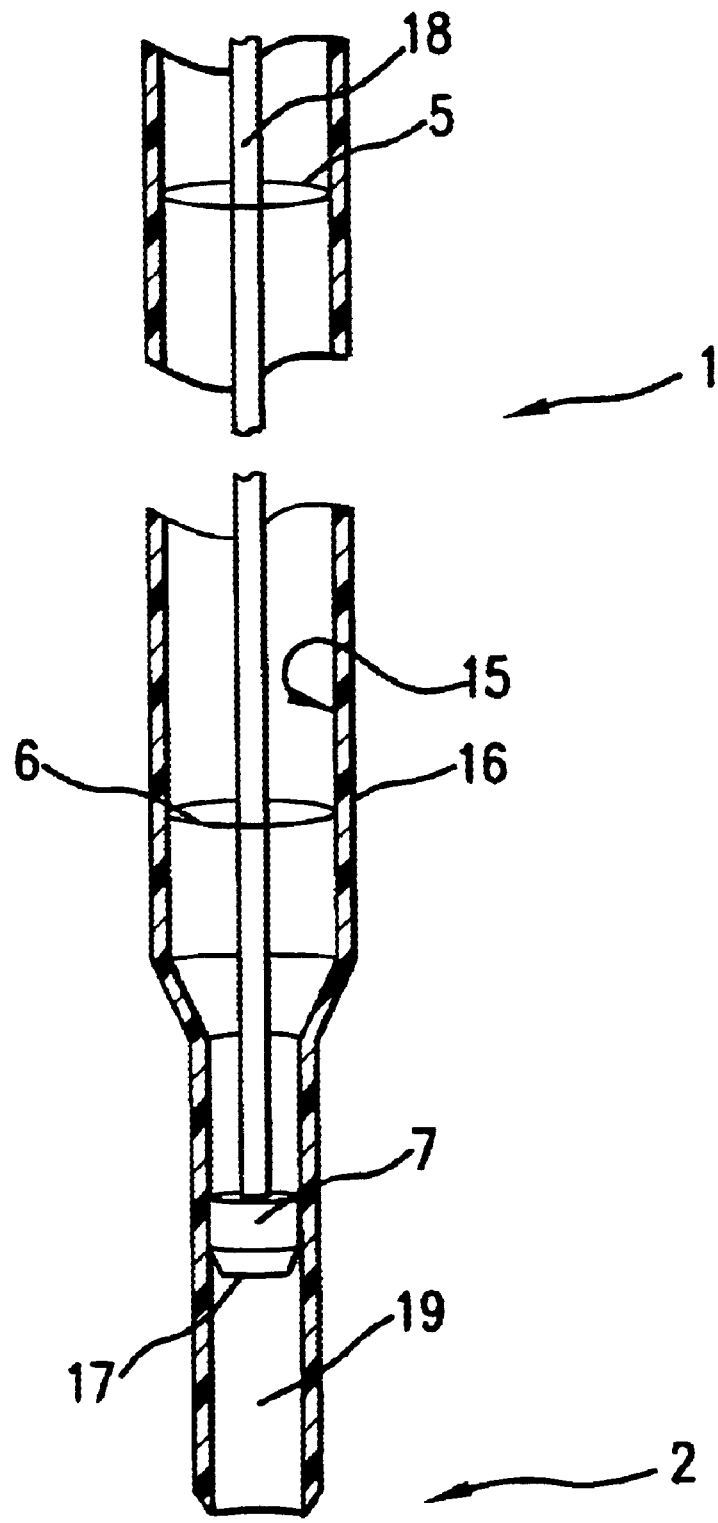
FIG. 5 is a schematic of the outer hollow rod with inner piston of the thief of the present invention retracted such that a cavity is created.

FIG. 2 is an example of the adjustable means or piston 9 that is to be inserted into the outer hollow rod 1. Piston 9 has a rod 18, and a plunger 7 at the bottom end of the piston 9. This plunger 7 forms a seal with the inner surface 15 of outer hollow rod 1. This plunger 7 has two shallow grooves opposite each other up the long axis of the plunger to allow air and gas to escape when the thief is in operation. The piston 9 contains a disk 6 of diameter a. This disk 6 acts as a guide for the piston 9 in outer hollow rod 1. The top end of the piston 9 consists of a second disk 5 with diameter a. This second disk 5 also acts as a guide to keep the inner shaft centered. The position of piston 9 within the outer hollow rod is adjustably fixable such that a cavity 19 of predetermined size is created. FIG. 5 is a schematic of the piston 9 in the retracted position so that a cavity 19 of a predetermined size is created. The cavity 19 is defined by the space between the bottom end 2 of outer hollow rod 1 and the lower surface 17 of the plunger 7.

FIG. 3 is a schematic of the outer hollow rod 1 with the piston 9 inside of 1. The thief probe is designed such that the piston 9 is moveable to adjust for the desired sample size. At the top of the piston 9 there is a handle 3 which is used to turn the piston 9 to lock piston 9 in place. Where it will be locked will determine the volume of the cavity created. In FIG. 3 this locking mechanism is depicted as a worm/screw type mechanism. Inner surface 15 of outer hollow rod 1 has grooves 11 to allow twisting of the worm/screw mechanism. FIG. 4 is a bisection of the worm/screw type locking mechanism. Each thread 13 of the mechanism can be labeled 12 to show the volume of cavity created by twisting to that point. For example in FIG. 4 each thread corresponds to 0.5 cc volume of cavity created. To create a cavity that will hold 1 cc of sample, the handle 3 is twisted until it reaches the tread that indicated 1 cc.

In an alternative embodiment, the locking mechanism is a series of teeth 8 (FIG. 1) wherein the teeth are spaced apart such that when a rod 4 attached to the top of the piston 9 is locked in a specific tooth 8, a set volume of cavity is created. The rod 4 protrudes about 0.5 to 1.0 cm further than the disks. By lifting at handle 3, rod 4 can be set into any of the teeth 8. In the closed position, the rod 4 is positioned in between the lowest teeth 8. By adjusting rod 4 into different teeth 8, different sample sizes can be captured. For example, the lowest tooth creates a cavity of 0.5 cc, the next tooth, 1.0 cc, and so forth. There can be any number of teeth, preferably greater than 3, and the spacing between the teeth is approximately 1.0–1.3 cm, preferably 1.25 cm depending on the sample size to be created. Rod 4 is an optional feature which is only necessarily present in this embodiment.

All parts of the apparatus of the present invention can be made of any solid material which can withstand the pressure of being inserted into the bulk material to be sampled. Examples of materials which can be used include, preferably, stainless steel. The plunger 7, disk 6 and disk 5 are preferably stainless steel or teflon.

In one embodiment, the thief of the present invention operates by inserting the piston 9 into the outer hollow rod 1. In the preferred embodiment, the thief, in the closed position, is inserted into the sample just above the area to be sampled. In the closed position (0.0 cc), the plunger 7 is flush against bottom end 2. The plunger 7 has a lower surface 17 which closes the bottom end 2 of outer hollow rod 1. The handle 3 is then rotated so that the cavity opens to a volume not less than 1 cc greater than the desired sample volume. The number of twists will depend on the desired sample size to be sampled. Once the cavity is open, the thief is manually lowered further into the sample by the operator. This process causes the material to be sampled to become compacted within the bottom end 2 of the thief. The thief is withdrawn and the sample is partially ejected to a setting representing the desired sample volume and discarded to remove any contamination from other areas of the powder bed. The remaining sample is ejected into a sample bottle for testing.

In an alternative embodiment, the thief is in the closed position when the rod 4 is positioned on the lowest tooth 8. In the closed position, the plunger 7 is flush against bottom end 2. The thief, in the closed position, is inserted into the material to be sampled. The bottom end 2 is positioned just above the area of the material to be sampled. At this point the thief is opened. To open the thief, the handle 3 is retracted by the operator. The rod 4 is then inserted between the tooth 8 which corresponds with the desired sample size. After rod 4 is locked in place, the operator then manually lowers the thief into the material. This process causes the material to be sampled to become compacted within the bottom end 2 of the thief. The thief is withdrawn and the sample is partially ejected to a setting representing the desired sample volume and discarded to remove any contamination from other areas of the powder bed. The remaining sample is ejected into a sample bottle for testing.

The design of the thief of the present invention minimizes any segregation or disturbance of the blend material. By first inserting the thief into the material just above the area to be sampled, there is no disturbance to the area to be sampled. When the opened thief is then lowered into the area to be sampled, the sample is representative of the true homogeneity. By such operation, the sample does not suffer from any disturbances or segregation usually caused by insertion of thieves of the prior art into sample material.

Conventional state of the art thieves are structurally different from the thief of the present invention. Conventional thieves consist of an hollow inner sleeve and an hollow outer sleeve. The inner sleeve has a cavity of a specific predetermined size. The size will depend on the size of the sample to be taken. The outer hollow sleeve has an opening or hole. The inner sleeve can be rotated within the outer sleeve so that the cavity lines up with the hole or opening. This is considered the open position. When the cavity and hole are not lined up this is considered the closed position. This conventional thief operates by inserting the thief into a sample in the closed position. When the thief is at the desired location in the sample, the hollow inner sleeve is rotated so that the thief is in the open position. This allows sample to fall through the hole into the cavity which may be assisted by rotation in the open position. The thief is then closed and withdrawn from the material. The thief is disassembled to remove the sample from the cavity.

The following examples are merely illustrative and not intended to limit the scope of the present invention in any manner.

EXAMPLES

In the following examples, a thief in accordance with the present invention is compared to conventional thieves. Several products are selected for these tests as follows:

Terazosin 1, from Geneva Pharmaceuticals is a low dose, direct blend product.

Alendronate Sodium 5, a development batch from Geneva Pharmaceuticals, is a direct blend with recognized sampling problems.

Thioridazine 200, from Geneva Pharmaceuticals, is a high dose, granulated product.

Perphenazine/ATP 2/25, from Geneva Pharmaceuticals, is a granulated product which historically has a recognized sampling problem.

Metoprolol 100, from Geneva Pharmaceuticals, is a product with a recognized sampling problem. Only a portion of the metoprolol product is granulated resulting in a portion of the sample being denser than the rest. This causes a larger difference in particle size between the granulated and ungranulated portions of the sample.

Each sample is assayed by the current analytical methodology for the specific product. Then samples from different locations in the container are assayed. The mean is the average of the 10 samples. The range is the highest value to lowest. The RSD is determined by the equation:

$$RSD = \frac{\sqrt{\frac{\sum (X - \overline{X})^2}{n-1}}}{\overline{X}} \times 100$$

Where X=assay value of each sample; $\overline{X}$=mean assay; and n=the number of samples.

State-of-the-art thief I ("SATI"), available from Globe Pharmaceuticals, is a side sampling thief which has an inner cylinder into which varying sized sample ports are inserted enclosed by an outer rotating sleeve. The sleeve has holes that align with the sampling ports, allowing adjacent powder to flow into the sampling ports. Rotating the sleeve to its closed position traps the samples in the ports. The closed thief is withdrawn and the samples are removed from the thief. State-of-the-art thief II ("SATII"), a modification on the Globe thief, is smaller in diameter and may create less disturbance in the material to be sampled. In Examples 1–5, the thief of the present invention does not have a beveled tip. The thief of Example 6 does have a beveled tip.

Example 1

The following blend uniformity results are measured for Terazosin 1:

| Thief | mean | range | RSD |
| --- | --- | --- | --- |
| SATII | 91.5% | 90.8–92.8% | 0.6% |
| SATI | 91.1% | 90.2–92.2% | 0.7% |
| Present Invention | 91.4% | 89.8–92.2% | 0.7% |

Terazosin I theoretically poses a sampling challenge because it is a low dose, direct blend product. However, here all three thieves show similar blend uniformity results.

Example 2

A developmental batch of Alendronate Sodium 5 is sampled for blend uniformity using all 3 thieves and the following results are obtained:

| Thief | mean | range | RSD |
| --- | --- | --- | --- |
| SATII | 92.6% | 83.9–104.1% | 7.7% |
| SATI | 90.7% | 84.6–109.7% | 8.0% |
| Present invention | 89.4% | 86.9–94.6% | 3.1% |

The above results show more consistency from sample to sample by using the thief of the present invention. Alendronate sodium is a direct blend product. High values obtained with SATI and SATII may be due to sampling phenomena, Example 3

The following are the results of sampling with Thioridazine 200:

| Thief | mean | range | RSD |
| --- | --- | --- | --- |
| SATII | 101.4% | 100.3–102.3% | 0.6% |
| SATI | 100.5% | 97.7–101.9% | 1.7% |
| Present Invention | 100.5% | 99.5–102.6% | 1.1% |

Thioridazine 200 is a high dose, granulated blend and therefore it was not expected to present any real sampling challenges. The above results show no sampling problems with any of the 3 thieves.

Example 4

The following results are obtained for Perphenazine/ATP 2/25:

| Perphenazine-Thief | mean | range | RSD |
|---|---|---|---|
| SATII | 96.4% | 94.8–97.6% | 1.0% |
| SATI | 97.6% | 95.3–100.7% | 1.7% |
| Present Invention | 96.2% | 93.7–99.2% | 1.5% |

| Amitriptyline-Thief | mean | range | RSD |
|---|---|---|---|
| SATIl | 97.8% | 95.8–98.8% | 1.0% |
| SATI | 98.5% | 96.4–101.4% | 1.7% |
| Present Invention | 97.8% | 95.7–100.2% | 1.2% |

Although a granulated product, the Perphenazine/ATP product family has historically been prone to sampling error. However, as shown above, no error is evident in the sampling study with any of the thieves. The results show that the thief of the present invention works just as well as the thieves of the prior art.

Example 5

An experimental batch of Metoprolol 100, was initially sampled with the prior art thief and resampled with the thief of the present invention:

| Thief | mean | range | RSD |
|---|---|---|---|
| SATII | 100.9% | 78.9–108.7% | 8.3% |
| Present invention | 96.3% | 91.0–105.2% | 4.1% |

Results show better results with the thief of the present invention. Metoprolol poses an unusual sampling problem because only the active ingredient containing portion of the metoprolol product is granulated, resulting in that portion of the sample being coarser and denser than the rest. This causes differing flow properties between the granulated and ungranulated portions of the sample and often results in sampling-caused error.

Example 6

A second experimental batch of Metoprolol 100 is investigated for blend uniformity failure using a thief of the present invention with a beveled tip. The results are shown below:

| Thief | mean | range | RSD |
|---|---|---|---|
| SATII | 101.7% | 86.9–112.2% | 7.2% |
| Present Invention | 101.5% | 98.0–108.3% | 2.9% |

I claim:

1. A sample thief for sampling a pharmaceutical blend comprising:
   (a) an outer hollow rod having a top open end and a bottom open end, wherein the bottom open end is beveled;
   (b) a piston having a plunger at the bottom open end;
      wherein said plunger has a lower surface, and
      wherein the position of said piston within the outer hollow rod is adjustably fixable by an adjustable means such that a cavity of predetermined size is created, and
      wherein said cavity is defined by the space between said bottom open end of the outer hollow rod and the lower surface of said plunger.

2. A sample thief according to claim 1 wherein said outer hollow rod has an inner surface and an outer surface, wherein said plunger forms a seal with the inner surface of the outer hollow rod.

3. A sample thief according to claim 1 wherein the adjustable means comprises threads.

4. A sample thief according to claim 1 wherein the adjustable means is a series of teeth on the outer hollow rod and a protrusion or rod on the piston which can be locked with the teeth of the outer hollow rod.

5. A process to sample a pharmaceutical blend comprising:
   (a) inserting a sample thief according to claim 1 into a pharmaceutical blend such that the bottom open end of the thief is located just above the area of the pharmaceutical blend to be sampled;
   (b) adjusting the adjustable means so that a cavity greater than the size of the desired volume of sample is created;
   (c) lowering the thief further into the pharmaceutical blend;
   (d) removing the thief from the pharmaceutical blend;
   (e) ejecting the excess sample to a predetermined point; and
   (f) collecting the sample.

* * * * *